United States Patent [19]
Gall

[11] 3,992,408
[45] Nov. 16, 1976

[54] PHTHALIMIDO ALKANONE, ETHYLENE KETALS
[75] Inventor: Martin Gall, Kalamazoo, Mich.
[73] Assignee: The Upjohn Company, Kalamazoo, Mich.
[22] Filed: Aug. 6, 1975
[21] Appl. No.: 602,322

Related U.S. Application Data
[62] Division of Ser. No. 505,342, Sept. 12, 1974, Pat. No. 3,910,946.

[52] U.S. Cl. .......................... 260/326 N; 260/326 A
[51] Int. Cl.² ....................................... C07D 209/48
[58] Field of Search .................... 260/326 N, 326 A Primary Examiner—Lewis Gotts
Assistant Examiner—S. P. Williams
Attorney, Agent, or Firm—Hans L. Berneis

[57] ABSTRACT

Phthalimides of the Formula

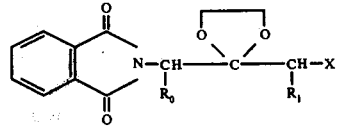

wherein X is $NH_2$, $N(CH_3)_2$, Cl or Br and $R_0$ and $R_1$ are hydrogen, methyl or ethyl are disclosed as intermediates in the preparation of benzodiazepines.

4 Claims, No Drawings

PHTHALIMIDO ALKANONE, ETHYLENE KETALS

This is a division of application Ser. No. 505,342, filed Sept. 12, 1974 now U.S. Pat. No. 3,910,946.

BACKGROUND OF THE INVENTION

FIELD OF THE INVENTION

This invention is directed to new organic compounds and is particularly concerned with novel 6-phenyl-4H-imidazo[1,2-a][1,4]benzodiazepines, novel intermediates and processes for the production thereof.

The novel compounds and the processes of production therefor can be illustratively represented as follows:

Scheme I

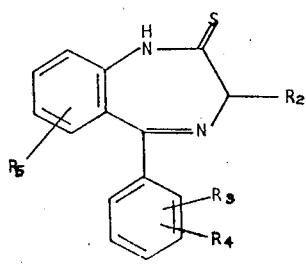

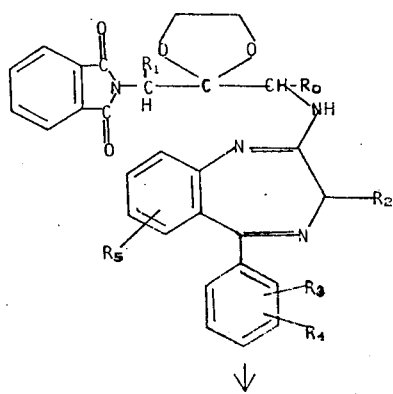

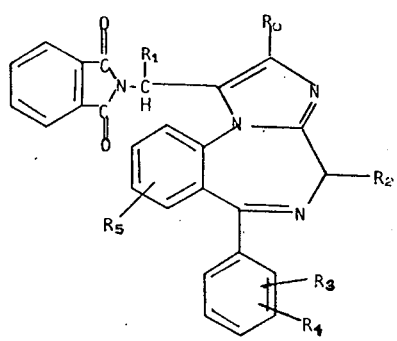

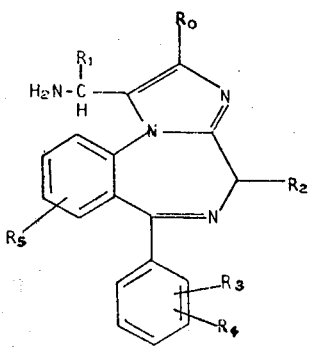

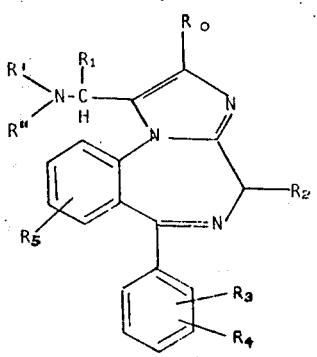

Alternatively, the synthetic steps for compound V can be carried out as follows:

Scheme II

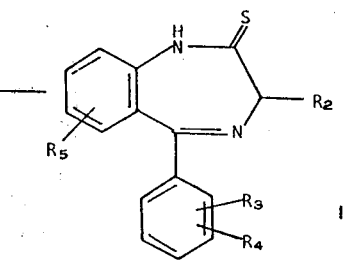

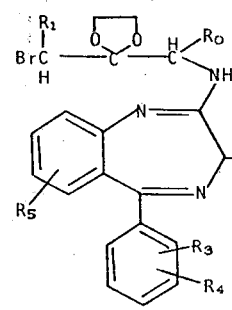

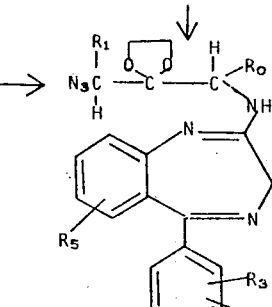

3
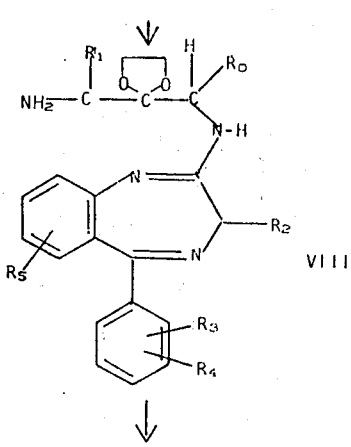
VIII
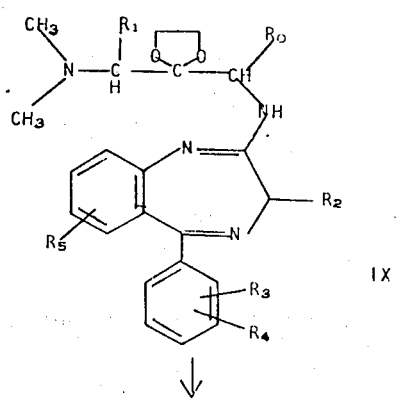
IX
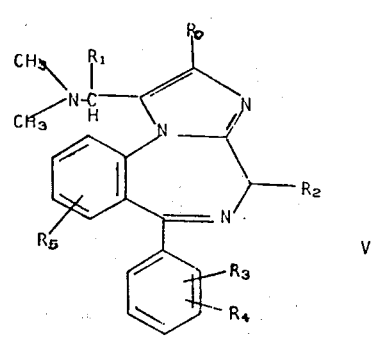
V
or
Scheme III
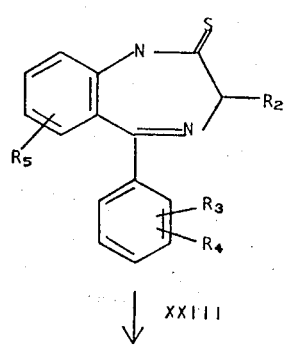
I
↓ XXIII
4
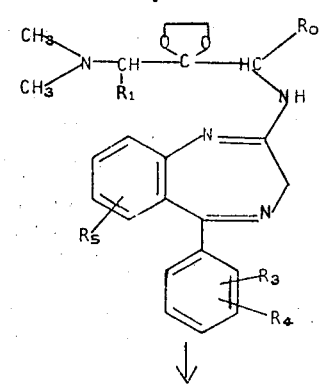
IX
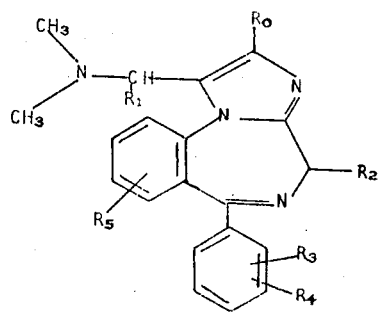
V
The reagents used in the foregoing syntheses were prepared (for scheme I) by the method shown below:
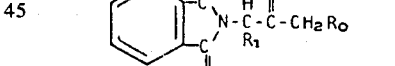
X
$R_0$=H, CH$_3$ or CH$_5$
↓
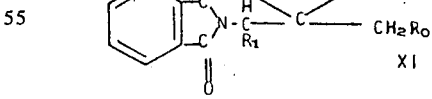
XI
↓
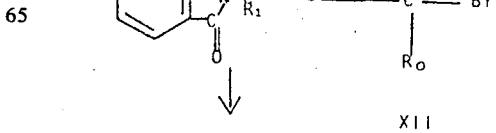
XII
↓

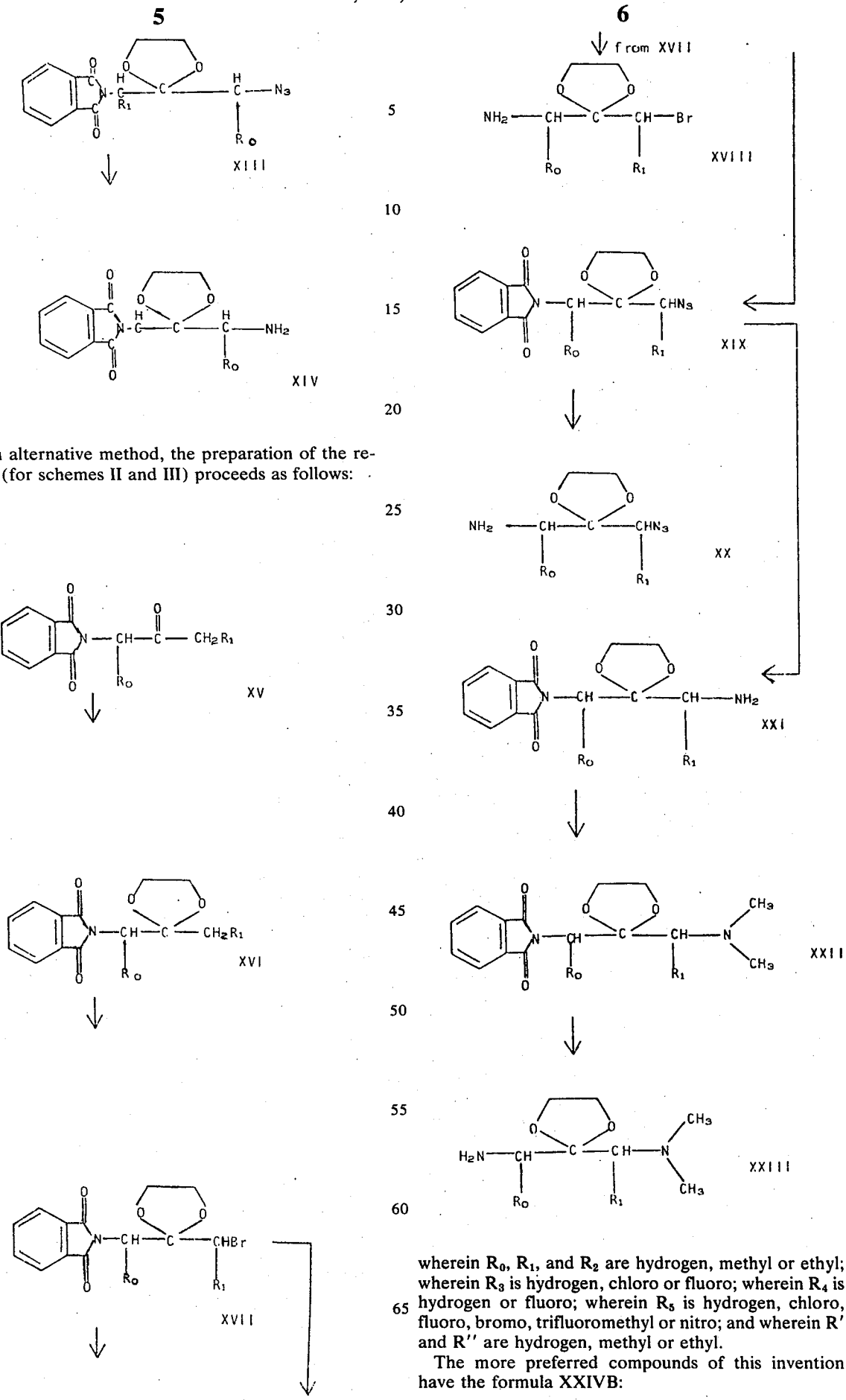

In an alternative method, the preparation of the reagents (for schemes II and III) proceeds as follows:

wherein $R_0$, $R_1$, and $R_2$ are hydrogen, methyl or ethyl; wherein $R_3$ is hydrogen, chloro or fluoro; wherein $R_4$ is hydrogen or fluoro; wherein $R_5$ is hydrogen, chloro, fluoro, bromo, trifluoromethyl or nitro; and wherein $R'$ and $R''$ are hydrogen, methyl or ethyl.

The more preferred compounds of this invention have the formula XXIVB:

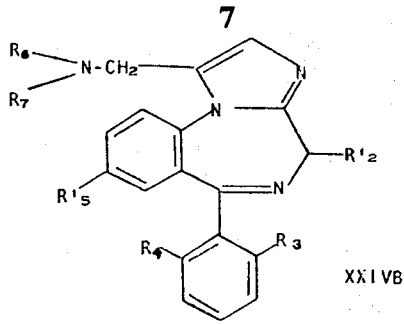

XXIVB wherein $R_6$, $R_7$, and $R_2''$ are hydrogen or methyl; wherein $R_3$ and $R_4$ are defined as above; and wherein $R'_5$ is chloro, fluoro or trifluoromethyl, and the pharmacologically acceptable acid addition salts thereof.

The most preferred compounds are of the formula XXIVC:

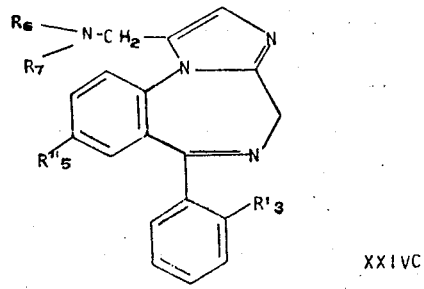

XXIVC wherein $R_6$ and $R_7$ are defined as above; $R'_3$ is hydrogen or chloro; $R''_5$ is chloro or fluoro; and the pharmacologically acceptable acid addition salts thereof.

The process for the production of compounds of formula XXIV comprises: heating a compound of formula I with the novel reagent XIV to yield compound II; reacting compound II with sulfuric acid to obtain compound III; reacting compound III with hydrazine to obtain compound IV and alkylating compound IV with alkylhalides or formaldehyde, sodium cyanoborohydride and acetic acid, to give V, or alternatively reductively alkylating IV in the presence of a suitable catalyst to give a compound of formula XXIV. Compounds IV and V represent the partial scope of the final, desired compounds, otherwise identified as compounds of formula XXIV.

In a similar manner the desired final compounds can be prepared by reacting compound I with the intermediate compound XVIII to give compound VI; reacting compound VI with sodium azide to give compound VII; catalytically hydrogenating VII to give compound VIII; alkylating to give compound IX, and then heating compound IX to between 110° C and 200° C to give compound V, which is a final compound of the invention, encompassed by formula XXIV. Compound VII may be prepared directly by reacting compound I with the intermediate compound XX. Compound IX may also be prepared directly by reacting compound I with the intermediate XXIII (scheme III).

Other variations of these reaction schemes are possible, and will appear in examples. The examples will also show the production of the reactants used in this invention.

The new final compounds of formula XXIV and the pharmacologically acceptable acid addition salts thereof are essentially products which are useful in mammals to counteract anxiety and to produce tranquilization.

DESCRIPTION OF THE PREFERRED EMBODIMENT OF THE INVENTION

The tranquilization and sedative activity of the new compounds of formula XXIV and their pharmacologically acceptable acid addition salts was tested in mice as follows:

Chimney test: [Med. Exp. 4, 145 (1961)]: The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish.

Pedestal test: The untreated mouse leaves the pedestal in less than a minute to climb back to the floor of the standard mouse box. Tranquilized mice will stay on the pedestal for more than one minute.

Nicotine antagonism test: Mice in a group of 6 are injected with the test compound. Thirty minutes later the mice including control (untreated) mice are injected with nicotine salicylate (2 mg./kg.). The control mice show overstimulation, i.e., (1) running convulsions, followed by (2) tonic extensor fits; followed by (3) death.

TESTING FOR ANXIETY ANTAGONISM

INTRODUCTION

It is generally accepted that one result of psychic stress is an increase in plasma corticosteroid levels. (See Table I). A number of investigators have shown that many psychoactive compounds have an effect on plasma corticosteroid levels in both the unstressed [V. Marc and P. L. Marselli. J. Pharm. Pharmac. 21, 785 (1969), S. Makela, E. Naatanen and U. K. Rinne. Acta Endocr. 32: 1 (1959), R. W. O. Sevy, E. A. Ohler and A. Weiner. Endocrinology 61: 45 (1957), S. Makela, E. Naatanen and U. K. Rinne Acta Endocr. 32: 1(1959)] and stressed animal [R. W. O. Sevy, E. A. Ohler and A. Weiner. Endocrinology 61: 45 (1957) C. W. H. Harvard, V. F. Saldanka, R. Bird, and R. Gardner. J. Endocr. 52: 79 (1972) A. Pekkarinen and M. Haataja. "The inhibiting effect of tricyclic antidepressant drugs on the increase of the corticosteroid content by reserpine in the rat plasma." Congress of International Collegium of Neuropsychopharmacologium, Copenhagan, Aug. 14–17, 1972.]. Therefore corticosteroid levels were studies in stressed rats as a possible test parameter for psychoactive drugs.

METHODS AND MATERIALS:

General procedure -- Male rats weighing 120–140 gm each were arranged five to a cage in the animal room and left that way overnight. Between 8:00 and 9:00 a.m. the following day the rats were injected with the drug intraperitoneally and left in their cages. After one hour the groups of rats were placed into different cages and moved to a room where a radio was playing loudly. Thirty minutes later the rats were given a sham intraperitoneal injection. The animals were anesthetized with halothane 10 minutes later, the heart exposed surgically and 3.5–5ml of blood was drawn from the right ventricle into a heparinized 5cc plastic syringe using a 20 gauge needle. The blood samples were stored on ice until centrifugation (1000g) within 20 minutes. The plasma was stored at 4° C until assayed (within 3 hours). Assay procedure -- The corticosteroid levels were determined fluorometrically using a procedure adapted from that proposed by V. H. T. James et al, British Med. J. 2, 310 [1971]. Two ml. of plasma is extracted with 15 ml. of methylene chloride by shaking for 10 minutes in a 50 ml. glass stoppered tube on a mechanical shaker. After the phases have been allowed to separate, the plasma layer is aspirated off and discarded. Reagent blanks (2 ml water) and standards (2 ml of 50 $\mu$g cortisol/100 ml water) are treated in the same manner. To develop fluorescence, 5 ml, of the methylene chloride extract is added to 3 ml of sulfuric acid: ethanol (7:3) in -[15-ml. glass stoppered tube and shaken vigorously for 20–30 seconds. The acid layer is transferred to a cuvette and the fluorescence is measured 13 minutes after mixing. The activation and emission wave-lengths are 470 nm and 530 nm, respectively. The results are calculated as $\mu$g corticosteroids/100-ml. plasma =

$$\frac{(\text{fluorescence of test}) - (\text{fluorescence of blank}) \times 50 \ \mu g/100 \ ml.}{(\text{fluorescene of standard}) - (\text{fluorescence of blank})}$$

TABLE I

Change in Corticosteroids Level in Response to Stress

| Treatment | Corticosteroid Level ($\mu$g/100 ml)* |
|---|---|
| Untreated | 17.9 ± 5.0 |
| Injection of vehicle - no stress applied | 19.3 ± 2.7 |
| Injection of vehicle - stress applied | 77.5 ± 17.4 |

*Sampled 1 hour after injection

TABLE II

Corticosteroids Levels and Duration of Stress

| Length of Stress Period before Sampling | Corticosteroid Level ($\mu$g/100 ml) |
|---|---|
| ½ hr. | 98 ± 3.5 |
| 1 hr. | 107 ± 13.5 |
| 2 hr. | 16.5 ± 5.3 |

The groups of rats were isolated for one hour between injection and stress period.

TABLE III

Corticosteroid Level in Response to Diazepam (Valium) in Stressed Rats

| Dose (mg/kg) | Corticosteroid Level ($\mu$g/100 ml) |
|---|---|
| 0 | 89.8 ± 12.2 |
| 1.25 | 79.8 ± 21.3 NS |
| 2.50 | 57.1 ± 22.5 NS |
| 5.0 | 28.3 ± 10.7 p<.01 |
| 10.0 | 21.7 ± 2.7 p<.01 |

Librium also antagonized increases in corticosteroid levels (at about 0.5 the potency of diazepam). Chlorpromazine (Merck index 8th ed., page 250) and Imipramine (Merck Index 8th ed., page 562) are practically inactive in this test.

The compound, 8-chloro-1-[(dimethylamino)methyl]-6-phenyl-4H-imidazo[1,2-a][1,4]benzodiazepine, of this invention is superior to Valium on equal dosages.

The pharmaceutical forms contemplated by this invention include pharmaceutical compositions suited for oral, parenteral, and rectal use, e.g., tablets, powder packets, cachets, dragees, capsules, solutions, suspensions, sterile injectible forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Water and oils, e.g., coconut oil, sesame oil, safflower oil, cottonseed oil, peanut oil may be used for preparing solutions or suspensions of the active drug. Sweetening, coloring, and flavoring agents may be added.

For mammals and birds, food premixes with starch, oatmeal, dried fishmeat, fishmeal, flour and the like can be prepared.

In feed for chicken, swine or cattle from 25–25,000 mg. of compounds of formula XXIV including formulae IV and V, or acid addition salts thereof are incorporated per ton of feed.

As tranquilizers, the compounds of formula XXIV (including XXIVa and XXIVb) can be used in unit dosages of 0.2 mg.–25 mg./kg., preferably between 0.5 and 10 mg./kg, in oral or injectable preparations as described above, to alleviate tension and anxieties in mammals, or birds, such as e.g., occurs when animals are in travel. For larger mammals the lower dosages are indicated. For the treatment of anxiety in mammals, unit dosage forms of 1 to 30 mg./kg. are indicated. In large mammals 25 kg. and over, 2 to 20 mg. unit dosage is considered satisfactory.

The starting materials of formula I of this invention, substituted or unsubstituted 1,3-dihydro-5-phenyl-2H-1,4-benzodiazepine-2-thiones, are described by G. A. Archer and L. H. Sternbach [J. Org. Chem. 29, 231 (1964) and U.S. Pat. No. 3,422,091]. These compounds (I) are made by the reaction of the known substituted or unsubstituted 1,3-dihydro-5-phenyl-2H-1,4-benzodiazepin-2-ones by heating with phosphorus pentasulfide in pyridine for about 45 minutes (Archer et al., ibid.). The following compounds of formula I are representative starting materials:

7-chloro-1,3-dihydro-5-(o-chlorophenyl)-2H-1,4-benzodiazepine-2-thione;
7-chloro-1,3-dihydro-5-phenyl-2H-1,4-benzodiazepine-2-thione;
7-fluoro-1,3-dihydro-5-phenyl-2H-1,4-benzodiazepine-2-thione;
7-fluoro-1,3-dihydro-5-(2,6-difluorophenyl)-2H-1,4-benzodiazepine-2-thione;
7-chloro-1,3-dihydro-5-(o-fluorophenyl)-2H-1,4-benzodiazepine-2-thione;
7-fluoro-1,3-dihydro-5-(o-chlorophenyl)-2H-1,4-benzodiazepine-2-thione;
7-chloro-1,3-dihydro-5-(2,6-difluorophenyl)-2H-1,4-benzodiazepine-2-thione;
7-trifluoromethyl-1,3-dihydro-5-(o-chlorophenyl)-2H-1,4-benzodiazepine-2-thione;
7-trifluoromethyl-1,3-dihydro-5-phenyl-2H-1,4-benzodiazepine-2-thione;
7-nitro-1,3-dihydro-5-phenyl-2H-1,4-benzodiazepine-2-thione;
7-nitro-1,3-dihydro-5-(o-chlorophenyl)-2H-1,4-benzodiazepine-2-thione;
8-chloro-1,3-dihydro-5-phenyl-2H-1,4-benzodiazepine-2-thione;

9-trifluoromethyl-1,3-dihydro-5-(o-fluorophenyl)-2H-1,4-benzodiazepine-2-thione;
1,3-dihydro-5-(o-chlorophenyl)-2H-1,4-benzodiazepine-2-thione;
6-fluoro-1,3-dihydro-5-(o-fluorophenyl)-2H-1,4-benzodiazepine-2-thione;
7-chloro-1,3-dihydro-3-ethyl-5-phenyl-2H-1,4-benzodiazepine-2-thione;
7-chloro-1,3-dihydro-3-methyl-5-(o-chlorophenyl)-2H-1,4-benzodiazepine-2-thione;
7-nitro-1,3-dihydro-3-methyl-5-(o-chlorophenyl)-2H-1,4-benzodiazepine-2-thione;
7-chloro-1,3-dihydro-3-methyl-5-(2,6-difluorophenyl)-2H-1,4-benzodiazepine-2-thione;
7-bromo-1,3-dihydro-3-methyl-5-(o-chlorophenyl)-2H-1,4-benzodiazepine-2-thione;
7-trifluoromethyl-1,3-dihydro-3-methyl-5-(o-chlorophenyl)-2H-1,4-benzodiazepine-2-thione; and the like.

In carrying out the process of this invention, a starting compound of formula I and a (3-phthalimidoacetonyl)amine, ethylene ketal is reacted together. In the preferred embodiment of this invention, the reaction is carried out in an organic solvent, inert in this reaction, e.g. in alkanols, such as methanol, ethanol, 1- or 2- propanol, n-butanol, tetrahydrofuran, dioxane or the like. Heating the reaction mixture between 40° C and its reflux temperature, as well as maintaining a nitrogen atmosphere, are preferred. The reaction period is between 6 to 48 hours, with 12 to 24 hours at 50° to 75° C preferred. The product II, 5-phenyl-2-[(3-phthalimidoacetonyl)amino]-3H-1,4-benzodiazepine, ethylene ketal thus obtained, is recovered and isolated by standard procedures, e.g., filtration (the compound II is not soluble in the cold solvent), chromatography and/or crystallization from solvent mixtures e.g. methanol/ethyl acetate, acetone, carbon tetrachloride/methanol, or the like.

Compound II, thus obtained, is treated with excess concentrated sulfuric acid at 20°–30° C (room temperature) in a nitrogen atmosphere for 6–24 hours. This reaction mixture is then quenched in cold water, adjusted to pH>8, and the resulting product III, a 1-phthalimidomethyl-6-phenyl-4H-imidazo[1,2-a][1,4]benzodiazepine, is recovered by extraction e.g. with chloroform, tetrahydrofuran, methylene chloride or the like. Purification of compound III is carried out by conventional methods.

Compound III is then reacted with an excess of hydrazine (1.5 to 10 mole equivalents of hydrazine per one mole equivalent of compound III) or hydrazine hydrate at temperatures from 20°–75°, preferably at room temperature (20° to 30° C), in ethanol under a nitrogen atmosphere. One to 24 hours reaction time is generally required. After the reaction is completed, the reaction mixture is filtered. The mother liquors containing the amino compound IV are redissolved in an organic solvent and the isolation and purification is made by treatment with mineral acid, generally hydrochloric acid to form the hydrochloride of IV which is further recrystallized to give the pure hydrochloride of IV, 1-(aminomethyl)-6-phenyl-4H-imidazo-[1,2-a][1,4]benzodiazepine hydrochloride.

Compound IV is alkylated by dissolving the free amine in a suitable solvent, preferably acetonitrile and treating the solution in a nitrogen atmosphere successively with formaldehyde (37% aqueous formalin) in a large excess and then sodium cyanoborohydride [NaBH$_3$CN]. The reaction mixture is then adjusted to a pH of 6.4 to 6.8 by addition dropwise of acetic acid dissolved in acetonitrile under continuous stirring. The thus-produced product V is recovered in the crude state by evaporating the reaction mixture in vacuo and is purified by chromatography, and/or recrystallization.

The monomethylated compound may be obtained by refluxing compound V with phenyl chloroformate and potassium or sodium bicarbonate in a suitable organic solvent, followed by refluxing with an alkali metal hydroxide.

Alternatively compounds of the formula XXIV may be obtained by treating IV with an aldehyde or ketone of from two to three carbon atoms followed by catalytic reduction of the resulting Schiff base in a suitable organic solvent.

Variations of these reactions can be made and the resulting products can then be converted by the processes shown above, to give the corresponding final compounds as illustrated by formula XXIV. These processes will subsequently be shown in examples. In the same manner the various reactants used for these reactions will be shown in the subsequent examples.

The following examples are illustrative of the processes and products of the present invention, but are not to be construed as limiting:

EXAMPLE 1

Phthalimidoacetone ethylene ketal

A solution of phthalimidoacetone 61.9 g (300 mmole) and ethylene glycol 18.9 g (300 mmole) in 300 ml of benzene in the presence of concentrated sulfuric acid (1 drop) is refluxed with stirring for 24 hours. An additional portion of ethylene glycol (18.9 g., 300 mmole) and p-toluenesulfonic acid (3 mg) is added and refluxing is continued for 65 hours. The reaction mixture is cooled in ice, washed with saturated sodium chloride solution and dried over anhydrous sodium sulfate. The benzene is removed in vacuo and the residue is crystallized from methanol to give 67 g (90%) of phthalimidoacetone, ethylene ketal as white prisms of melting point 92°–94° C.

EXAMPLE 2

(3-Phthalimidoacetonyl)bromide, ethylene ketal

A solution of phthalimidoacetone ethylene ketal (2.47 g, 10 mmole) in 10 ml of diethylene glycol is heated on a steambath. To this hot solution bromine (1.6 g, 10 mmole) is added dropwise under nitrogen. The reaction mixture is cooled to room temperature and is quenched in 20 ml hexane. To this mixture is added solid sodium carbonate followed by chloroform and ice water. The organic layer is separated and the aqueous layer is extracted 3 times with chloroform. The chloroform extracts are washed with water, dried over anhydrous sodium sulfate, and evaporated in vacuo. The residue is crystallized from ethyl acetate/hexane to afford 2 g (55%) of (3-phthalimidoacetonyl)bromide, ethylene ketal as white prisms of melting point 139°–141° C. An analytical sample has a melting point of 140°–141° C.

Anal. Calcd. for $C_{13}H_{12}BrNO_4$ C, 47.87; H, 3.71; N, 4.29; Br, 24.50; Found: C, 47.66; H, 3.60; N, 4.42; Br, 24.76.

EXAMPLE 3

(3-Phthalimidoacetonyl)azide, ethylene ketal

A suspension of (3-phthalimidoacetonyl)bromide, ethylene ketal (70.0 g, 210 mmole) and sodium azide (33.0 g, 504 mmole) in 25 ml. of dimethyl sulfoxide is heated on a steambath under nitrogen for 4 days. The above mixture is poured onto ice and extracted with chloroform (3×, 500 ml). The chloroform extract is washed with water (2×), saturated sodium chloride solution and dried over anhydrous sodium sulfate. Evaporation of chloroform in vacuo gives a white oil which on trituration with hexane crystallizes to afford 59 g, (95%) of (3-phthalimidoacetonyl)azide, ethylene ketal as white prisms of melting point 90.5°–92° C. An analytical sample recrystallized from ethyl acetate hexane has a melting point 92.5°–93.5° C.

Anal. Calcd. for $C_{13}H_{12}N_4O_4$, mw 288.27: C, 54.16; H, 4.20; N, 19.44; Found: C, 53.95; H, 4.23; N, 19.15.

EXAMPLE 4

(3-Phthalimidoacetonyl)amine, ethylene ketal

A solution of 11.52 g (40.0 mmole) of (3-phthalimidoacetonyl)azide, ethylene ketal in 250 ml of ethyl acetate is hydrogenated over 1 g of 10% palladium on charcoal at room temperature, and 50 psi for 2.5 hours. The above mixture is filtered, washed thoroughly with more ethyl acetate and evaporated in vacuo to afford 10 g (96%) of 3-(phthalimidoacetonyl)amine ethylene ketal as a white oil. This compound is used directly for the next step.

EXAMPLE 5

(3-Phthalimidocetonyl)dimethylamine, ethylene ketal

To a solution (3-phthalimidoacetonyl)amine, ethylene ketal (5.2 g, 20 mmole) and 37% formalin solution (6.4 g, 80 mmole) in 250 ml of methanol/ethylacetate (20:50 ml) mixture, is added 10% palladium on charcoal (5 g) as a catalyst. The resulting mixture is hydrogenated at room temperature under 50 psi pressure for 18 hours. The catalyst is filtered off, washed thoroughly with more methanol, and the methanol is evaporated in vacuo, to afford 5 g (86%) of white oil, which crystallizes to afford (3-phthalimidoacetonyl)dimethylamine, ethylene ketal of melting point 123°–125° C.

Anal. Calcd. for $C_{15}H_{18}N_2O_4$, mw 290.31: C, 62.05; H, 6.25; N, 9.65; Found: C, 61.62; H, 6.45; N, 9.54.

EXAMPLE 6

1-Phthalimidobutanone

To a stirred suspension of potassium phthalimide (5.0 g, 0.027 mmole) in 25 ml of dimethylformamide is added, dropwise, 3.80 g (0.025 mmole) of 1-bromobutanone. The mixture is heated for 10 hours at 80° C under nitrogen and then 150 ml of chloroform is added. The resulting mixture is poured into 30 ml of water and the organic layer is separated and washed with 10 ml of 0.2N sodium hydroxide. The resulting chloroform and dimethylformamide solution is dried over anhydrous sodium sulfate, and evaporated in vacuo to give 1-phthalimidobutanone.

EXAMPLE 7

1-Phthalimidobutanone; ethylene ketal

In the manner given in Example 1, 1-phthalimidobutanone is refluxed with ethylene glycol and a catalytic amount of p-toluenesulfonic acid in benzene to give 1-phthalimidobutanone, ethylene ketal.

EXAMPLE 8

1-Phthalimido-3-bromo-2-butanone, ethylene ketal

In the manner given in example 2, 1-phthalimidobutanone, ethylene ketal in diethylene glycol is heated with bromine to give 1-phthalimido-3-bromo-2-butanone, ethylene ketal.

EXAMPLE 9

1-Phthalimido-3-azido-2-butanone, ethylene ketal

In the manner given in example 3, 1-phthalimido-3-bromo-2-butanone ethylene ketal in dimethyl sulfoxide is heated with sodium azide to give 1-phthalimido-3-azido-2-butanone, ethylene ketal.

EXAMPLE 10

1-Phthalimido-3-amino-2-butanone, ethylene ketal

In the manner given in example 4, 1-phthalimido-3-azido-2-butanone, ethylene ketal in ethyl acetate is reduced with molecular hydrogen and palladium on charcoal to give 1-phthalimido-3-amino-2-butanone, ethylene ketal.

EXAMPLE 11

1-Phthalimido-3-(dimethylamino)-2-butanone ethylene ketal

In the manner given on example 5, 1-phthalimido-3-amino-2-butanone ethylene ketal and an aqueous 37% formalin solution in methanol/ethyl acetate mixture is reductively methylated with molecular hydrogen and palladium on charcoal to give 1-phthalimido-3-(dimethylamino)-2-butanone, ethylene ketal.

EXAMPLE 12

7-Chloro-5-phenyl-2-[(3-phthalimidoacetonyl)amino]-3H-1,4-benzodiazepine, ethylene ketal A suspension of 7-chloro-1,3-dihydro-5-phenyl-2H-1,4-benzodiazepine-2-thione (1.44 g; 5 mmole) and (3-phthalimidoacetonyl)amine, ethylene ketal, (4.5 g, 17 mmole) in 40 ml of absolute ethanol is heated at 60° C. overnight under nitrogen. The above solution on cooling gives 750 mg of a white solid of melting point 220°–229° C, which is discarded. The filtrate I is concentrated in vacuo and the residue is chromatographed on a silica gel column using 3% methanol-97% chloroform to afford 950 mg. of 7-chloro-5-phenyl-2-[(3-phthalimidoacetonyl)amino]-3H-1,4-benzodiazepine, ethylene ketal. An analytical sample recrystallized from acetone, has a melting point of 142°–145° C.

Anal. Calcd. for $C_{28}H_{23}ClN_4O_4$: C, 65.30; H, 4.50; N, 10.85; Cl, 6.88; Found: C, 65.10; H, 4.55; N, 10.85; Cl, 6.79.

EXAMPLE 13

7-Chloro-5-(o-chlorophenyl)-2-[(3-phthalimidoacetonyl)amino]-3H-1,4-benzodiazepine, ethylene ketal A suspension of 7-chloro-1,3-dihydro-5-(o-chlorophenyl)-2H-1,4-benzodiazepine-2-thione (18 g, 56 mmole) and (3-phthalimidoacetonyl)amine, ethylene ketal (28.88 g, 112mmole) in 800 ml. of absolute ethanol is heated on a steambath, under nitrogen for 24 hours. The above mixture is then evaporated to dryness in vacuo to give 27 g (84%) of 7-chloro-5-(o-chlorophenyl)-2-[(3-phthalimidoacetonyl)amino]-3H-1,4-benzodiazepine, ethylene ketal as a buff-colored compound of melting point 180°–190° C. An analytical sample recrystallized from methanol ethyl acetate has a melting point of 200°–202° C.

Anal. Calcd. for $C_{28}H_{22}Cl_2N_4O_4$: C, 61.21; H, 4.04; N, 10.20; Cl, 12.90; Found: C, 61.42; H, 4.11; N, 9.93; Cl, 12.57.

EXAMPLE 14

7-Chloro-5-(o-chlorophenyl)-2-[(3-phthalimido-1-methylacetonyl)amino]-3H-1,4-benzodiazepine, ethylene ketal In the manner given in example 12 a suspension of 7-chloro-1,3-dihydro-5-(o-chlorophenyl)-2H-1,4-benzodiazepine-2-thione (9 g, 28 mmole) and 1-phthalimido-3-amino-2-butanone ethylene ketal (15.4 g, 56.0 mmole) in 400 ml. of absolute ethanol is heated on a steambath under nitrogen for 24 hours. After the usual work-up and isolation procedure, one obtains 7-chloro-5-(o-chlorophenyl)-2-[(3-phthalimido-1-methylacetonyl)amino]-3H-1,4-benzodiazepine ethylene ketal.

EXAMPLE 15

7-Chloro-5-(2,6-difluorophenyl)-2-[(3-phthalimidoacetonyl)amino]-3H-1,4-benzodiazepine, ethylene ketal In the manner given in Example 12, 7-chloro-1,3-dihydro-5-(2,6-difluorophenyl)-2H-1,4-benzodiazepine-2-thione is heated with (3-phthalimidoacetonyl)amine, ethylene ketal in ethanol to give 7-chloro-5-(2,6-difluorophenyl)-2-[(3-phthalimidoacetonyl)amino]-3H-1,4-benzodiazepine, ethylene ketal.

EXAMPLE 16

7-Nitro-5-phenyl-2-[(3-phthalimidoacetonyl)amino]-3H-1,4-benzodiazepine, ethylene ketal In the manner given in Example 12, 7-nitro-1,3-dihydro-5-phenyl-2H-1,4-benzodiazepine-2-thione is heated with (3-phthalimidoacetonyl)amine, ethylene ketal in ethanol to give 7-nitro-5-phenyl-2-[(3-phthalimidoacetonyl)amino]-3H-1,4-benzodiazepine, ethylene ketal.

EXAMPLE 17

7-Nitro-5-(o-chlorophenyl)-2-[(3-phthalimidoacetonyl)amino]-3H-1,4-benzodiazepine, ethylene ketal In the manner given in example 12, 7-nitro-1,3-dihydro-5-(o-chlorophenyl)-2H-1,4-benzodiazepine-2-thione is heated with (3-phthalimidoacetonyl)amine, ethylene ketal in ethanol to give 7-nitro-5-(o-chlorophenyl)-2-[(3-phthalimidoacetonyl)amino]-3H-1,4-benzodiazepine, ethylene ketal.

EXAMPLE 18

7-Trifluoromethyl-5-phenyl-2-[(3-phthalimidoacetonyl)amino]-3H-1,4-benzodiazepine, ethylene ketal In the manner given in example 12, 7-trifluoromethyl-1,3-dihydro-5-phenyl-2H-1,4-benzodiazepine-2-thione is heated with (3-phthalimidoacetonyl)amine, ethylene ketal in ethanol to give 7-trifluoromethyl-5-phenyl-2-[(3-phthalimidoacetonyl)amino]-3H-1,4-benzodiazepine, ethylene ketal.

EXAMPLE 19

7-Trifluoromethyl-5-(o-chlorophenyl)-2-[(3-phthalimidoacetonyl)amino]-3H-1,4-benzodiazepine, ethylene ketal In the manner given in example 12, 7-trifluoromethyl-(o-chlorophenyl)-2H-1,4-benzodiazepine-2-thione is heated with (3-phthalimidoacetonyl)amine, ethylene ketal in ethanol to give 7-trifluoromethyl-5-(o-chlorophenyl)-2-[(3-phthalimidoacetonyl)amino]-3H-1,4-benzodiazepine, ethylene ketal.

In the manner given in Example 12, other compounds of formula II can be produced, such as: 7-nitro-5-(2,6-difluorophenyl)-2-[(3-phthalimidoacetonyl)amino]-3H-1,4-benzodiazepine, ethylene ketal; 7-fluoro-5-(2,6-difluorophenyl)-2-[(3-phthalimidoacetonyl)amino]-3H-1,4-benzodiazepine, ethylene ketal;
7-fluoro-5-phenyl-2-[(3-phthalimidoacetonyl)amino]-3H-1,4-benzodiazepine, ethylene ketal;
7-fluoro-5-(o-chlorophenyl)-2-[(3-phthalimidoacetonyl)amino]-3H-1,4-benzodiazepine, ethylene ketal;
7-fluoro-5-(o-fluorophenyl)-2-[(3-phthalimidoacetonyl)amino]-3H-1,4-benzodiazepine, ethylene ketal;
6-chloro-5-phenyl-2-[(3-phthalimidoacetonyl)amino]-3H-1,4-benzodiazepine, ethylene ketal;
8-bromo-5-(o-chlorophenyl)-2-[(3-phthalimidoacetonyl)amino]-3H-1,4-benzodiazepine, ethylene ketal;
5-(o-chlorophenyl)-2-[(3-phthalimidoacetonyl)amino]-3H-1,4-benzodiazepine, ethylene ketal;
7-trifluoromethyl-5-(2,6-difluorophenyl)-2-[(3-phthalimidoacetonyl)amino]-3H-1,4-benzodiazepine, ethylene ketal; 7-trifluoromethyl-5-(o-fluorophenyl)-2-[(3-phthalimidoacetonyl)amino]-3H-1,4-benzodiazepine, ethylene ketal; and the like.

EXAMPLE 20

8-Chloro-1-(phthalimidomethyl)-6-phenyl-4H-imidazo[1,2-a][1,4]benzodiazepine

A suspension of 7-chloro-5-phenyl-2-[(3-phthalimidoacetonyl)amino]-3H-1,4-benzodiazepine, ethylene ketal (15 g, 29 mmole) in 50 ml. of concentrated sulfuric acid is stirred at room temperature under nitrogen for 18 hours. This is then quenched in cold water, neutralized with 10% aqueous sodium hydroxide, and extracted with chloroform (400 ml, 4X). The chloroform solution is washed with water, saturated aqueous sodium chloride solution, dried over anhydrous sodium sulfate and evaporated to dryness in vacuo to afford a yellow oil. This is crystallized from ethyl acetate/hexane to afford 5.6 g (42.5%) of 8-chloro-1-(phthalimidomethyl)-6-phenyl-4H-imidazo[1,2-a][1,4]benzodiazepine of melting point 236°–240° C. An analytical sample recrystallized from ethyl acetate/hexane has a melting point of 240°–242° C.

Anal. Calcd. for $C_{26}H_{17}ClN_4O_2$: C, 68.95; H, 3.78; N, 12.37; Cl, 7.83; Found: C, 68.87; H, 4.22; N, 12.35; Cl, 7.63.

EXAMPLE 21

8-Chloro-1-(phthalimidomethyl)-6-(o-chlorophenyl)-4H-imidazo[1,2-a][1,4]benzodiazepine A suspension of 7-chloro-5-(o-chlorophenyl)-2-[(3-phthalimidoacetonyl)amino]-3H-1,4-benzodiazepine, ethylene ketal (800 mg, 1.5 mmole) is stirred in 3 ml. of concentrated sulfuric acid at room temperature under nitrogen for 20 hours. The above mixture is quenched in ice-water, neutralized with 5% aqueous sodium hydroxide, and extracted with chloroform (50 ml, 3X). The chloroform extract is washed with water, saturated aqueous sodium chloride solution, dried over anhydrous sodium sulfate, and evaporated to dryness in vacuo leaving a white oil. This is crystallized from ethyl acetate/hexane to give 430 mg. (61%) 8-chloro-1-(phthalimidomethyl)-6-(o-chlorophenyl)-4H-imidazo[1,2-a][1,4]benzodiazepine. An analytical sample recrystallized from ethyl acetate/hexane has a melting point of 218°–220° C.

Anal. calcd for $C_{26}H_{16}Cl_2N_4O_2$, mw 487.33: C, 64.08; H, 3.31; N, 11.50; Cl, 14.35; Found: C, 63.90; H, 3.35; N, 11.26; Cl, 14.06.

EXAMPLE 22

8-Chloro-1-(phthalimidomethyl)-2-methyl-6-(o-chlorophenyl)-4H-imidazo[1,2-a][1,4]benzodiazepine In the manner given in example 20 a suspension of 7-chloro-5-(o-chlorophenyl)-2-[(3-phthalimido-1-methylacetonyl)amino]-3H-1,4-benzodiazepine, ethylene ketal in concentrated sulfuric acid is stirred at room temperature under nitrogen for 18 hours and the reaction mixture poured onto ice, treated with base and the product isolated to give 8-chloro-1-(phthalimidomethyl)-2-methyl-6-(o-chlorophenyl)-4H-imidazo[1,2-a][1,4]benzodiazepine.

EXAMPLE 23

8-Nitro-1-(phthalimidomethyl)-6-phenyl-4H-imidazo[1,2-a][1,4]benzodiazepine

In the manner given in Example 20, 7-nitro-5-phenyl-2-[(3-phthalimidoacetonyl)amino]-3H-1,4-benzodiazepine, ethylene ketal is treated with concentrated sulfuric acid, then quenched to give, after neutralization, 8- nitro-1-(phthalimidomethyl)-6-phenyl-4H-imidazo[1,2-a][1,4]benzodiazepine.

EXAMPLE 24

8-Nitro-1-(phthalimidomethyl)-6-(o-chlorophenyl)-4H-imidazo[1,2-a][1,4]benzodiazepine In the manner given in Example 20, 7-nitro-5-(o-chlorophenyl)-2-[(3-phthalimidoacetonyl)amino]-3H-1,4-benzodiazepine, ethylene ketal is treated with concentrated sulfuric acid, then quenched to give, after neutralization, 8-nitro-1-(phthalimidomethyl)-6-(o-chlorophenyl)-4H-imidazo-[1,2-a][1,4]benzodiazepine.

EXAMPLE 25

8-Trifluoromethyl-1-(phthalimidomethyl)-6-phenyl-4H-imidazo[1,2-a][1,4]benzodiazepine In the manner given in Example 20, 7-trifluoromethyl-5-phenyl-2-[(3-phthalimidoacetonyl)amino]-3H-1,4-benzodiazepine, ethylene ketal is treated with concentrated sulfuric acid, then quenched to give after neutralization, 8-trifluoromethyl-1-(phthalimidomethyl)-6-phenyl-4H-imidazo-[1,2-a][1,4] benzodiazepine.

EXAMPLE 26

8-Trifuoromethyl-1-(phthalimidomethyl)-6-(o-chlorophenyl)-4H-imidazo[1,2-a][1,4]benzodiazepine In the manner given in example 20, 7-trifluoromethyl-5-(o-chlorophenyl)-2-[(3-phthalimidoacetonyl)amino]-3H-1,4-benzodiazepine, ethylene ketal is treated with concentrated sulfuric acid, then quenched to give, after neutralization, 8-trifluoromethyl-1-(phthalimidomethyl)-6-(o-chlorophenyl)-4H-imidazo[1,2-a][1,4]benzodiazepine.

EXAMPLE 27

8-Chloro-1-(phthalimidomethyl)-6-(2,6-difluorophenyl)-4H-imidazo[1,2-a][1,4-benzodiazepine In the manner given in example 20, 7-chloro-5-(2,6-difluorophenyl)-2-[(3-phthalimidoacetonyl)amino]-3H-1,4-benzodiazepine, ethylene ketal is treated with concentrated sulfuric acid, then quenched to give after neutralization, 8-chloro-1-(phthalimidomethyl)-6-(2,6-difluorophenyl)-4H-imidazo[1,2-a][1,4]benzodiazepine.

In the manner given in example 20, other 1-(phthalimidomethyl)-6-phenyl-4H-imidazo[1,2-a][1,4]benzodiazepines can be synthesized. Representative compounds, thus obtained, include:
8-fluoro-(1-phthalimidomethyl)-6-(2,6-difluorophenyl)-4H-imidazo[1,2-a][1,4]benzodiazepine;
8-fluoro-1-(phthalimidomethyl)-6-phenyl-4H-imidazo[1,2-a]-[1,4]benzodiazepine;
8-fluoro-1-(phthalimidomethyl)-6-(o-chlorophenyl)-4H-imidazo[1,2-]-[1,4]benzodiazepine;
8-fluoro-1-(phthalimidomethyl)-6-(o-fluorophenyl)-4H-imidazo[1,2-a][1,4]benzodiazepine;
7-chloro-1-(phthalimidomethyl)-6-phenyl-4H-imidazo[1,2-a][1,4]benzodiazepine;
8-bromo-1-(phthalimidomethyl)-6-(o-chlorophenyl)-4H-imidazo[1,2-a][1,4]benzodiazepine;
1-(phthalimidomethyl)-6-(o-chlorophenyl)-4H-imidazo-[1,2-a][1,4]-benzodiazepine;
8-trifluoromethyl-1-(phthalimidomethyl)-6-(2,6-difluorophenyl)-4H-imidazo[1,2-a][1,4]benzodiazepine;
8-trifluoromethyl-1-(phthalimidomethyl)-6-(o-fluorophenyl)-4H-imidazo[1,2-a][1,4]benzodiazepine; and the like.

EXAMPLE 28

8-Chloro-1-(aminomethyl)-6-phenyl-4H-imidazo-[1,2-a][1,4]benzodiazepine dihydrochloride A suspension of 8-chloro-1-(phthalimidomethyl)-6-phenyl-4H-imidazo[1,2-a][1,4]benzodiazepine (1 g, 2 mmole) and hydrazine hydrate (500 mg, 10 mmole) in 25 ml. of absolute ethanol is stirred at room temperature under nitrogen for 18 hours. The white solid (byproduct 1) which separated is removed by filtration. The filtrate from above is evaporated to dryness and the residue is dissolved in chloroform. The chloroform solution is washed with water, saturated sodium chloride solution, dried over anhydrous sodium sulfate, and concentrated in vacuo, to give a white oil. This oil is dissolved in ethyl acetate and to this is added methanolic hydrogen chloride. The resulting solution is concentrated to a small volume and cooled, to afford 830 mg.

(95% of 8-chloro-1-(aminomethyl)-6-phenyl-4H-imidazo[1,2-a][1,4]benzodiazepine dihydrochloride. An analytical sample is recrystallized from methanol ethyl acetate and has a melting point of 275°–280° C.

Anal. Calcd. for $C_{18}H_{15}ClN_4 \cdot 2HCl \cdot 1/2 H_2O$: C, 53.42; H, 4.48; N, 13.85; Cl, 26.27; Found: C, 53.53; H, 4,34; N, 14.05; Cl, 26.17.

EXAMPLE 29

8-Chloro-1-(aminomethyl)-6-(o-chlorophenyl)-4H-imidazo[1,2-a][1,4]benzodiazepine A suspension of 8-chloro-1-(phthalimidomethyl)-6-(o-chlorophenyl)-4H-imidazo[1,2-a][1,4]benzodiazepine (2.14g, 4.4 mmole) and hydrazine hydrate (1 g, 22 mmole) in 75 ml. of absolute ethanol is stirred at room temperature under nitrogen for 20 hours. The white solid which precipitates is removed by filtration. The ethanol solution is evaporated to dryness in vacuo and the residue is dissolved in chloroform. The chloroform solution is washed with water, then with saturated sodium chloride solution, dried over anhydrous sodium sulfate, and evaporated in vacuo to give 1.56 g. (100%) of yellow oil. This oil is alkylated without any purification [example 37].

EXAMPLE 30

8-Chloro-1-(aminomethyl)-2-methyl-6-(o-chlorophenyl)-4H-imidazo[1,2-a][1,4]benzodiazepine In the manner given in Example 28, a suspension of 1.00 mmole of 8-chloro-1-(phthalimido)methyl-2-methyl-6-(o-chlorophenyl)-4H-imidazo[1,2-a][1,4]benzodiazepine is treated with 5.00 mmole of hydrazine hydrate in 12 ml. of absolute ethanol at room temperature for 18 hours to afford, after removal of the phthalazine by-product, 8-chloro-1-aminomethyl-2-methyl-6-(o-chlorophenyl)-4H-imidazo[1,2-a][1,4]benzodiazepine.

EXAMPLE 31

8-Nitro-1-(aminomethyl)-6-phenyl-4H-imidazo-[1,2-a][1,4]benzodiazepine

In the manner given in Example 28, 8-nitro-1-(phthalimidomethyl)-6-phenyl-4H-imidazo[1,2-a][1,4]-benzodiazepine is reacted at room temperature with hydrazine hydrate, dissolved in ethanol to give 8-nitro-1-(aminomethyl)-6-phenyl-4H-imidazo[1,2-a][1,4]benzodiazepine.

EXAMPLE 32

8-Nitro-1-(aminomethyl)-6-(o-chlorophenyl)-4H-imidazo[1,2-a][1,4]benzodiazepine

In the manner given in Example 28, 8-nitro-1-(phthalimidomethyl)-6-(o-chlorophenyl)-4H-imidazo[1,2-a][1,4]benzodiazepine is reacted at room temperature with hydrazine hydrate, dissolved in ethanol to give 8-nitro-1-(aminomethyl)-6-(o-chlorophenyl-4H-imidazo[1,2-a][1,4]-benzodiazepine.

EXAMPLE 33

8-Trifluoromethyl-1-(aminomethyl)-6-phenyl-4H-imidazo[1,2-a][1,4]benzodiazepine

In the manner given in Example 28, 8-trifluoromethyl-1-(phthalimidomethyl)-6-phenyl-4H-imidazo[1,2-a][1,4]benzodiazepine is reacted at room temperature with hydrazine hydrate, dissolved in ethanol, to give 8-trifluoromethyl-1-(aminomethyl)-6-phenyl-4H-imidazo[1,2-a][1,4]benzodiazepine.

EXAMPLE 34

8-Trifluoromethyl-1-(aminomethyl)-6-(o-chlorophenyl)-4H-imidazo[1,2-a][1,4]benzodiazepine In the manner given in Example 28, 8-trifluoromethyl-1-(phthalimidomethyl)-6-(o-chlorophenyl)-4H-imidazo[1,2-a][1,4]benzodiazepine is reacted at room temperature with hydrazine hydrate, dissolved in ethanol, to give 8-trifluoromethyl-1-(aminomethyl)-6-(o-chlorophenyl)-4H-imidazo-[1,2-a][1,4]benzodiazepine.

EXAMPLE 35

8-Chloro-1-(aminomethyl)-6-(2,6-difluoromethyl)-4H-imidazo[1,2-a][1,4]benzodiazepine In the manner given in Example 28, 8-chloro-1-(phthalimidomethyl)-6-(2,6-difluorophenyl)-4H-imidazo-[1,2-a][1,4]benzodiazepine is reacted at room temperature with hydrazine hydrate, dissolved in ethanol, to give 8-chloro-1-(aminomethyl)-6-(2,6-difluorophenyl-4H-imidazo-[1,2-a][1,4]benzodiazepine.

In the manner given in Example 28, other 1-(aminomethyl)-6-phenyl-4H-imidazo[1,2-a][1,4]-benzodiazepines can be prepared. Representative compounds include:
8-fluoro-1-(aminomethyl)-6-(2,6-difluoromethyl)-4H-imidazo-[1,2-a][1,4]benzodiazepine;
8-fluoro-1-(aminomethyl)-6-phenyl-4H-imidazo[1,2-a][1,4]-benzodiazepine;
8-fluoro-1-(aminomethyl)-6-(o-chlorophenyl)-4H-imidazo-[1,2-a][1,4]benzodiazepine;
8-fluoro-1-(aminomethyl)-6-(o-fluorophenyl)-4H-imidazo-[1,2-a][1,4]benzodiazepine;
7-chloro-1-(aminomethyl)-6-(o-chlorophenyl)-4H-imidazo-[1,2-a][1,4]benzodiazepine;
8-bromo-1-(aminomethyl)-6-(o-chlorophenyl)-4H-imidazo-[1,2-a][1,4]benzodiazepine;
1-(aminomethyl)-6-(o-chlorophenyl)-4H-imidazo[1,2-a][1,4]benzodiazepine;
8-trifluoromethyl-1-(aminomethyl)-6-(2,6-difluorophenyl)-4H-imidazo[1,2-a][1,4]benzodiazepine;
8-trifluoromethyl-1-(aminomethyl)-6-(o-fluorophenyl)-4H-imidazo[1,2-a][1,4]benzodiazepine; and the like.

EXAMPLE 36

8-Chloro-1-[(dimethylamino)methyl]-6-phenyl-4H-imidazo[1,2-a][1,4]benzodiazepine A stirred solution of 8-chloro-1-(aminomethyl)-6-phenyl-4H-imidazo[1,2-a][1,4]benzodiazepine (1.42 g, 4.3 mmole) in 20 ml. of acetonitrile, under nitrogen, is treated successively with 37% aqueous formaldehyde (2.2 ml) and sodium cyanoborohydride ($NaBH_3CN$) (550 mg). This mixture is treated dropwise, with a solution of 0.2 ml. of acetic acid in 2 ml. of acetonitrile over a period of 1 hour and 30 minutes. [The addition is continued until the pH of the reaction mixture is between 6.4 – 6.8]. The mixture is stirred for 15 minutes at ambient temperature and concentrated in vacuo. The residue is treated with cold water saturated with sodium chloride and extracted with chloroform (5- ml., 3X). The chloroform solution is washed with water and saturated sodium chloride solution, then dried over anhydrous sodium sulfate, and concentrated in vacuo to give a yellow oil. This oil is chromatographed over silica gel by eluting with 2% methanol-98% chloroform mixtures to afford 700 mg. (47% of 8-chloro-1-[(dimethylamino)methyl]-6-phenyl-4H-imidazo-[1,2-a][1,4]benzodiazepine. An analytical sample recrystallizes from ethyl acetate/hexane has a melting point of 181°–182° C.

Anal. Calcd. for $C_{20}H_{19}ClN_4$: C, 68.46; H, 5.46; N, 15.97; Cl, 10.10; Found: C, 68.50; H, 5.50; N, 15.92; Cl, 10.37.

EXAMPLE 37

8-chloro-1-[(dimethylamino)methyl]-6-(o-chlorophenyl)-4H-imidazo[1,2-a][1,4]benzodiazepine, dihydrobromide and monohydrobromide A stirred solution of 8-chloro-1-(aminomethyl)-6-(o-chlorophenyl)-4H-imidazo[1,2-a][1,4]benzodiazepine (4.70 g, 12.9 mmole) in 60 ml. of dry acetonitrile, under nitrogen, is treated successively with 37% aqueous formaldehyde (6.6 ml) and sodium cyanoborohydride (1.65 g). This mixture is treated dropwise, over a period of 1 hour and 30 minutes, with a solution of acetic acid (0.6 ml) in acetonitrile (6 ml) and kept at ambient temperature for 15 minutes at which time the mixture is concentrated in vacuo. The residue is mixed with 90 ml of methanol and 25% aqueous ethylene diamine (60 ml) and refluxed for 45 minutes. The mixture is then diluted with cold water, saturated with sodium chloride and extracted with chloroform (100 ml, 4 times). The chloroform solution is first washed with water, followed by a saturated salt solution, then dried over anhydrous sodium sulfate, and finally, evaporated in vacuo to give 5.5 g (crude) oil. A portion of this oil is crystallized from methanol/ether mixtures as a monohydrobromide derivative of 8-chloro-1-[(dimethylamino)methyl]-6-(o-chlorophenyl)-4H-imidazo[1,2-a][1,4]-benzodiazepine (methanol solvate) of melting point 168°–171° C.

Anal. calcd for $C_{20}H_{18}Cl_2N_4 \cdot HBr \cdot H_2O \cdot 1/2CH_3OH$: C, 49.21; H, 4.63; N, 11.20; Halogen, 30.14; Found: C, 48.94; H, 4.62; N, 11.16; Halogen, 29.84.

A second compound, the dibromide, obtained after chromatography of the free base and reconversion to an HBr derivative (B) has a melting point 199°–201° C.
Anal calcd for $C_{20}H_{18}Cl_2N_4 \cdot 1\ 1/2HBr$ C, 47.41; H, 3.88; N, 11.06; Found: C, 47.51; H, 3.98; N, 11.31.

EXAMPLE 38

8-Chloro-6-(o-chlorophenyl)-1-[(dimethylamino)methyl]-2-methyl-4H-imidazo[1,2-a][1,4]benzodiazepine, monohydrobromide In the manner given in example 36, a stirred solution of 1.0 mmole of 8-chloro-1-aminomethyl-2-methyl-6-(o-chlorophenyl)-4H-imidazo[1,2-a][1,4]benzodiazepine in 5.0 ml. of acetonetrile under nitrogen is treated successively with 0.5 ml. of a 37% aqueous formalin solution, and sodium cyanoborohydride (100 mg). The mixture is treated dropwise with a solution of 0.05 ml. of acetic acid in 0.5 ml. of acetonitrile over a 30 minute period (until the pH is between 6.4 – 6.8). Following the procedure of example 36, the reaction mixture is worked up. The product is isolated as an oil which crystallizes as a monohydrobromide derivative from methanol/ethyl acetate mixture to afford 8-chloro-6-(o-chlorophenyl)-1-[(dimethylamino)methyl]-2-methyl-4H-imidazo-[1,2-a][1,4]benzodiazepine, monohydrobromide. The analytical sample has melting point 194°–197° C.

EXAMPLE 39

8-Nitro-1-[(dimethylamino)methyl]-6-phenyl-4H-imidazo[1,2-a][1,4]benzodiazepine

In the manner given in Example 36, 8-nitro-1-(aminomethyl)-6-phenyl-4H-imidazo[1,2-a][1,4]benzodiazepine in acetonitrile, is treated with formaldehyde, then with sodium cyanoborohydride and finally dropwise with acetic acid in acetonitrile to give 8-nitro-1-[(dimethylamino)methyl]-6-phenyl-4H-imidazo[1,2-a][1,4]benzodiazepine.

EXAMPLE 40

8-Nitro-1-[(dimethylamino)methyl]-6-(o-chlorophenyl)-4H-imidazo[1,2-a][1,4]benzodiazepine In the manner given in Example 36, 8-nitro-1-(aminomethyl)-6-(o-chlorophenyl)-4H-imidazo[1,2-a][1,4]-benzodiazepine, in acetonitrile, is treated with formaldehyde, then with sodium cyanoborohydride and finally dropwise with acetic acid in acetonitrile to give 8-nitro-1-[(dimethylamino)methyl]-6-(o-chlorophenyl)-4H-imidazo[1,2-a][1,4]-benzodiazepine.

EXAMPLE 41

8-Trifluoromethyl-1-[(dimethylamino)methyl]-6-phenyl-4H-imidazo[1,2-a][1,4]benzodiazepine In the manner given in Example 36, 8-trifluoromethyl-1-(aminomethyl)-6-phenyl-4H-imidazo[1,2-a][1,4]benzodiazepine in acetonitrile, is treated with formaldehyde, then with sodium cyanoborohydride and finally dropwise with acetic acid in acetonitrile to give 8-trifluoromethyl-1-[(dimethylamino)methyl]-6-phenyl-4H-imidazo[1,2-a][1,4]benzodiazepine.

EXAMPLE 42

8-Trifluoromethyl-1-[(dimethylamino)methyl]-6-(o-chlorophenyl)-4H-imidazo[1,2-a][1,4]benzodiazepine In the manner given in Example 36, 8-trifluoromethyl-1-(aminomethyl)-6-(o-chlorophenyl)-4H-imidazo[1,2-a][1,4]-benzodiazepine, in acetonitrile, is treated with formaldehyde, then with sodium cyanoborohydride, and finally dropwise with acetic acid in acetonitrile to give 8-trifluoromethyl-1-[(dimethylamino)methyl]-6-(o-chlorophenyl)-4H-imidazo[1,2-a][1,4]benzodiazepine.

EXAMPLE 43

8-Chloro-1-[(dimethylamino)methyl]-6-(2,6-difluorophenyl)-4H-imidazo[1,2-a][1,4]benzodiazepine In the manner given in Example 36, 8-chloro-1-(aminomethyl)-6-(2,6-difluorophenyl)-4H-imidazo[1,2-a][1,4]benzodiazepine in acetonitrile, is treated with formaldehyde, then with sodium cyanoborohydride and finally dropwise with acetic acid in acetonitrile to give 8-chloro-1-[(dimethylamino)methyl]-6-(2,6-difluorophenyl)-4H-imidazo-[1,2-a][1,4]benzodiazepine.

In the manner given in Example 36, other 1-[(dimethylamino)methyl]-6-phenyl-4H-imidazo[1,2-a][1,4]benzodiazepines can be produced. Representative compounds, thus produced, comprise:
8-fluoro-1-[(dimethylamino)methyl]-6-(2,6-difluorophenyl)-4H-imidazo[1,2-a][1,4]benzodiazepine;

8-fluoro-1-[(dimethylamino)methyl]-6-phenyl-4H-imidazo-[1,2-a][1,4]benzodiazepine;
8-fluoro-1-[(dimethylamino)methyl]-6-(o-chlorophenyl)-4H-imidazo[1,2-a][1,4]benzodiazepine;
8-fluoro-1-[(dimethylamino)methyl]-6-(o-fluorophenyl)-4H-imidazo[1,2-a][1,4]benzodiazepine;
7-chloro-1-[(dimethylamino)methyl]-6-(o-chlorophenyl)-4H-imidazo[1,2-a][1,4]benzodiazepine;
8-bromo-1-[(dimethylamino)methyl]-6-(o-chlorophenyl)-4H-imidazo[1,2-a][1,4]benzodiazepine;
1-[(dimethylamino)methyl]-6-(o-chlorophenyl)-4H-imidazo-[1,2-a][1,4]benzodiazepine;
8-trifluoromethyl-1-[(dimethylamino)methyl]-6-(2,6-difluoro-phenyl)-4H-imidazo[1,2-a][1,4]benzodiazepine;
8-trifluoromethyl-1-[(dimethylamino)methyl]-6-(o-fluorophenyl)-4H-imidazo[1,2-a][1,4]benzodiazepine; and the like.

EXAMPLE 44

8-Chloro-1-[(diethylamino)methyl]-6-phenyl-4H-imidazo[1,2-a][1,4]benzodiazepine

A stirred solution of 8-chloro-1-(aminomethyl)-6-phenyl-4H-imidazo[1,2-a][1,4]benzodiazepine (1.42 g, 4.3 mmole) in 20 ml. of acetonitrile under nitrogen is treated successively with acetaldehyde (1.5 ml) and sodium cyanoborohydride (NaBH₃CN) (550 mg). This mixture is treated dropwise, with a solution of 0.2 ml of acetic acid in 2 ml. of acetonitrile over a period of 1 hour and 30 minutes. [The addition is continued until the pH of the reaction mixture is between 6.4 - 6.8]. The mixture is stirred for 15 minutes at ambient temperature and concentrated in vacuo. The residue is treated with cold water saturated with sodium chloride and extracted with chloroform (5- ml., 3X). The chloroform solution is washed with water and saturated sodium chloride solution, then dried over anhydrous sodium sulfate, and concentrated in vacuo to give a yellow oil. This oil is chromatographed over silica gel by eluting with 2% methanol-98% chloroform mixtures to afford 8-chloro-1-[(diethylamino)methyl]-6-phenyl-4H-imidazo[1,2-a][1,4]benzodiazepine.

EXAMPLE 45

8-Chloro-1-[(dipropylamino)methyl]-6-phenyl-4H-imidazo[1,2-a][1,4]benzodiazepine A stirred solution of 8-chloro-1-(aminomethyl)-6-phenyl-4H-imidazo[1,2-a][1,4]benzodiazepine (1.42 g, 4.3 mmole) in 20 ml. of acetonitrile under nitrogen, is treated successively with propionaldehyde (1.94 ml) and sodium cyanoborohydride (NaBH₃CN) (550 mg). This mixture is treated dropwise, with a solution of 0.2 ml of acetic acid in 2 ml. of acetonitrile over a period of 1 hour and 30 minutes. [The addition is continued until the pH of the reaction mixture is between 6.4 – 6.8]. The mixture is stirred for 15 minutes at ambient temperature and concentrated in vacuo. The residue is treated with cold water saturated with sodium chloride and extracted with chloroform (5- ml., 3X). The chloroform solution is washed with water and saturated sodium chloride solution, then dried over anhydrous sodium sulfate, and concentrated in vacuo to give a yellow oil. This oil is chromatographed over silica gel by eluting with 2% methanol-98% chloroform mixtures to afford 8-chloro-1-[(dipropylamino)methyl]-6-phenyl-4H-imidazo[1,2-a][1,4]benzodiazepine.

EXAMPLE 46

8-Chloro-6-(o-chlorophenyl)-1-[(methylamino)methyl]-4H-imidazo[1,2-a][1,4]benzodiazepine.

A stirred suspension of 8-chloro-6-(o-chlorophenyl)-1-[(dimethylamino)methyl]-4H-imidazo[1,2-a][1,4]benzodiazepine (3.95 g, 10 mmole) and potassium bicarbonate (17 g, 17 mmole) in 280 ml. of chloroform is treated with phenyl chloroformate (12.97 g, 87 mmole) and refluxed for 50 hours. The resulting mixture is cooled, washed with water (100 ml) and the solvent is removed in vacuo. The residue is dissolved in 170 ml. of methanol and the resulting solution is treated with 100 ml. of 5.6 g of potassium hydroxide and 10 g of potassium bicarbonate. This mixture is stirred under nitrogen for 24 hours, acidified with concentrated hydrochloric acid, diluted with water, and extracted with 500 ml. of ether. The ether phase is dried over anhydrous sodium sulfate, and the ether is removed in vacuo. The thus obtained material is dissolved in a mixture of 800 ml. of ethanol and aqueous 50% potassium hydroxide (200 ml) and refluxed under nitrogen for 24 hours. This solution is treated with 200 ml. of concentrated hydrochloric acid and the ethanol is removed in vacuo. The remaining aqueous phase is extracted with ether, and the ether is discarded. The aqueous phase is then made basic, pH 9.0 and re-extracted with methylene chloride (800 ml). The methylene chloride is dried over anhydrous sodium sulfate and the solvent is removed in vacuo. The resulting oil is crystallized to give 8-chloro-6-(o-chlorophenyl)-1-[(methylamino)methyl]-4H-imidazo[1,2-a][1,4]benzodiazepine.

In the manner given in Example 46, other acid addition salts of 1-[(methylamino)methyl]-6-phenyl-4H-imidazo[1,2-a][1,4]benzodiazepines can be obtained. Representative compounds thus produced include:
8-chloro-1-[(methylamino)methyl]-6-phenyl-4H-imidazo[1,2-a][1,4]benzodiazepine;
8-nitro-1-[(methylamino)methyl]-6-phenyl-4H-imidazo[1,2-a][1,4]benzodiazepine;
8-nitro-1-[(methylamino)methyl]-6-(o-chlorophenyl-4H-imidazo[1,2-a][1,4]benzodiazepine;
8-trifluoromethyl-1[(methylamino)methyl]-6-phenyl-4H-imidazo[1,2-a][1,4]benzodiazepine;
8-trifluoromethyl-1-[(methylamino)methyl]-6-(o-chlorophenyl)-4H-imidazo[1,2-a][1,4]benzodiazepine;
8-fluoro-1-[(methylamino)methyl]-6-(o-fluorophenyl)-4H-imidazo[1,2-a][1,4]benzodiazepine;
8-chloro-1-[(methylamino)methyl]-6-(2,6difluorophenyl)-4H-imidazo[1,2-a][1,4]benzodiazepine;
8-fluoro-1-[(methylamino)methyl]-6-(2,6-difluorophenyl)-4H-imidazo[1,2-a][1,4]benzodiazepine;
8-fluoro-1-[(methylamino)methyl]-6-(o-chlorophenyl)-4H-imidazo[1,2-a][1,4]benzodiazepine;
8-bromo-1-[(methylamino)methyl]-6-(o-chlorophenyl)-4H-imidazo[1,2-a][1,4]benzodiazepine;
7-chloro-1-[(methylamino)methyl]-6-(o-chlorophenyl)-4H-imidazo[1,2-a][1,4]benzodiazepine;
10-trifluoromethyl-1-[(methylamino)methyl]-6-(2,6-difluorophenyl)-4H-imidazo[1,2-a][1,4]benzodiazepine;
8-trifluoromethyl-1-[(methylamino)methyl]-6-(o-fluorophenyl)-4H-imidazo[1,2-a][1,4]benzodiazepine; and the like.

EXAMPLE 47

(3-bromoacetonyl)amine, ethylene ketal (XVII)

A solution of (3-phthalimidoacetonyl)bromide, ethylene ketal (50 mmole) (Example 2) in absolute ethanol is stirred with hydrazine hydrate (200 mmole) during 20 hours in a nitrogen atmosphere. The white solid which precipitates is filtered and washed with ethanol. The ethanol filtrate and washings are combined, and distilled in vacuo and the resulting residue is distilled at 56°–58° C/0.05 mm Hg. to give 6.2 g of (3-bromoacetonyl)amine, ethylene ketal as a viscous oil $n_D^{28} = 1.499$. NMR(CDCl$_3$), δ 4.10 (4H, singlet), 3.49 (2H, singlet), 3.00 (2H, singlet), 1.40–1.78 (2H, broad singlet).

EXAMPLE 48

7-Chloro-5-phenyl-2-[(3-bromoacetonyl)amino]-3H-1,4-benzodiazepine

A suspension of 7-chloro-1,3-dihydro-5-phenyl-2H-1,4-benzodiazepine-2-thione (400 mg., 1.5 mmole) and (3-bromoacetonyl) amine, ethylene ketal (900 mg., 4.5 mmole) in 30 ml. of absolute ethanol is heated at 60° for 18 hours while a stream of nitrogen is bubbled through the reaction mixture. After cooling to room temperature, the ethanol is taken off in vacuo to afford 500 mg. of yellow oil. This oil on trituration with anhydrous ether gives 200 mg. (30%) of white solid. The solid is filtered and the resulting filtrate is removed in vacuo. The residue is chromatographed over silica gel by eluting with 3% methanol-97% chloroform to afford 80 mg. (12%) of 7-chloro-5-phenyl-2-[(3-bromoacetonyl)amino)-3H-1,4-benzodiazepine. An analytical sample crystallizes from ethyl acetate/hexane and has a melting point of 206°-290° C.

Anal. Calcd for $C_{20}H_{19}BrClN_3O_2$ mw 448.73 C, 53.53; H, 4.27; N, 9.37; Br, 17.81; Cl, 7.9;

Found: C, 53.23; H, 4.27; N, 9.51; Br, 17.84; Cl, 7.37.

EXAMPLE 49

7-Chloro-5-phenyl-2-[(3-azidoacetonyl)amino]-3H-1,4-benzodiazepine, ethylene ketal A suspension of 7-chloro-5-phenyl-2-[(3-bromoacetonyl)amino]-3H-1,4-benzodiazepine ethylene ketal (10 mmole) and sodium azide (1.56 g, 24 mmole) in 25 ml. of dimethylsulfoxide is heated on a steam bath in a nitrogen atmosphere during 5 days. The mixture is then cooled, extracted with chloroform; the chloroform extracts are dried over anhydrous sodium sulfate and evaporated. The resulting product is recrystallized from ethyl acetate - Skellysolve B (hexanes) to give 7-chloro-5-phenyl-2-[(3-azidoacetonyl)amino]-3H-1,4-benzodiazepine, ethylene ketal, melting point 181.5°–182.5° C.

EXAMPLE 50

7-Chloro-5-phenyl-2-[[3-(dimethylamino)acetonyl]amino]-3H-1,4-benzodiazepine, ethylene ketal A solution of 7-chloro-5-phenyl-2-[(3-azidoacetonyl)amino]-3H-1,4benzodiazepine, ethylene ketal in ethyl acetate is hydrogenated in the presence of 10% palladium on charcoal catalyst at room temperature for 3 hours at 50 psi of hydrogen. The reaction mixture is filtered and the filtrate evaporated to give crude 7-chloro-5-phenyl-2[(3-aminoacetonyl)amino]-3H-1,4-benzodiazepine, ethylene ketal which was immediately treated in acetonitrile solution, with 37% aqueous formaldehyde and sodium cyanoborohydride, followed by acetic acid to give 7-chloro-5-phenyl-2-[[3-(dimethylamino)acetonyl]amino]-3H-1,4-benzodiazepine, ethylene ketal as an oil.

EXAMPLE 51

8-Chloro-1-[(dimethylamino)methyl]-6-phenyl-4H-imidazo[1,2-a][1,4]benzodiazepine A suspension of 7-chloro-5-phenyl-2-[[3-(dimethylamino)acetonyl]amino]-3H-1,4-benzodiazepine, ethylene ketal (1.5 mmole) is heated to 110 to 120° in diethylene glycol under nitrogen for 20 hours. The above mixture is cooled and evaporated to dryness in vacuo leaving behind a white oil. This is crystallized from ethyl acetate/hexane to give 8-chloro-1-[(dimethylamino)methyl]-6-phenyl-4H-imidazo]1,2-a][1,4]benzodiazepine of melting point 181°—182° C.

EXAMPLE 52 3-azidoacetonyl)amine, ethylene ketal

A suspension of (3-phthalimidoacetonyl)azide, ethylene ketal (Example 3)(16 g, 56 mmole) and hydrazine hydrate (12 g, 240 mmole) in 250 ml of absolute ethanol is stirred at room temperature under nitrogen overnight. A white precipitate separates and is removed by filtration. The filtrate is evaporated in vacuo and the residue is distilled under reduced pressure. The product distills at 60°—62°/0.03–0.10 mm Hg pressure to afford 4.2 g (48%) of (3-azidoacetonyl)amine, ethlene ketal as a clean white oil of $N_D^{27} = 1.481$.

Anal. Calcd. for $C_5H_{10}N_4O_2$, mw 158.17:
C, 37.96: H, 6.37; N, 35.43.
Found: C, 37.89; H, 6.30; N, 35.16.

Example 53

7-Chloro-5-phenyl2[(3-azidoacetonyl)amino]-3H-1,4-benzodiazepine, ethylene ketal A suspension of 7-chloro-1,3-dihydro-5-phenyl-2H-1,4-benzodiazepine-2-thione (0.143 g, 0.5 mmole) and (3-azidoacetonyl)amine, ethylene ketal (0.240 g, 1.5 mmole) in 10 ml. of absolute ethanol is heated at 60° C. for 4 hours while a stream of nitrogen is bubbled through the reaction mixture. After cooling to room temperature the reaction mixture is quenched in cold water and extracted with chloroform (3X, 50 ml.). The chloroform extract is washed with water, saturated sodium chloride solution and dried over anhydrous sodium sulfate. Evaporation of chloroform in vacuo and trituration of the residue with anhydrous ether affords 180 mg. (87%) of 7-chloro-5-phenyl-2-[(3-azidoacetonyl)amino]-3H-1,4-benzodiazepine, ethylene ketal of melting point 180°–185° C. An analytical sample was recrystallized from ethyl acetate/hexane and had a melting point of 181.5°–182.5° C.

Anal. Calcd. for $C_{20}H_{19}ClN_6O_2$, mw 410.87: C, 58.46; H, 4.66; N, 20.46; Cl, 8.63; Found: C, 58.41; H, 4.69; N, 20.38; Cl, 9.00.

This product is converted as in Examples 50 and 51 to the final product 8-chloro-1-[(dimethylamino)methyl]-4H-imidazo[1,2-a][1,4]benzodiazepine.

In the same manner shown in the alternative procedures, Examples 47 through 53, the other prior-described 1-[(dialkylamino)alkyl]-6-phenyl-4H-imidazo[1,2-a][1,4]benzodiazepines can be prepared.

Moreover the synthesis shown in the prior examples, when carried out with a 3-methyl-5-phenyl-1,3-dihydro-2H-1,4-benzodiazepine-2-thiones provide the corresponding 1-[(dialkylamino)alkyl]-4-methyl-6-phenyl-4H-imidazo[1,2-a]-[1,4]benzodiazepines, such as:
8-chloro-1-[(dimethylamino)methyl]-4-methyl-6-phenyl-4H-imidazo[1,2-a][1,4]benzodiazepine;
8-chloro-1-[(dimethylamino)methyl]-4-methyl-6-(o-chlorophenyl)-4H-imidazo[1,2-a][1,4]benzodiazepine;
8-nitro-1-[(dimethylamino)methyl]-4-methyl-6-phenyl-4H-imidazo[1,2-a][1,4]benzodiazepine;
8-nitro-1-[(dimethylamino)methyl]-4-methyl-6-(o-chlorophenyl)-4-H-imidazo[1,2-a][1,4]benzodiazepine;
8-trifluoromethyl-1-[(dimethylamino)methyl]-4-methyl-6-phenyl-4H-imidazo[1,2-a][1,4]benzodiazepine;
8-trifluoromethyl-1-[(dimethylamino)methyl]-4-methyl-6-(o-chlorophenyl)-4H-imidazo[1,2-a][1,4]benzodiazepine;
8-fluoro-1-[(dimethylamino)methyl]-4-methyl-6-(o-chlorophenyl)-4H-imidazo[1,2-a][1,4]benzodiazepine;
8-chloro-1-[(dimethylamino)methyl]-4-methyl-6-(2,6-difluorophenyl)-4H-imidazo[1,2-a][1,4]benzodiazepine;
8-fluoro-1-[(dimethylamino)methyl]-4-methyl-6-(2,6-difluorophenyl)-4H-imidazo[1,2-a][1,4]benzodiazepine;
8-bromo-1-[(dimethylamino)methyl]-4-methyl-6-(o-chlorophenyl)-4H-imidazo[1,2-a][1,4]benzodiazepine;
1-[(dimethylamino)methyl]-4-methyl-6-(o-chlorophenyl)-4H-imidazo[1,2-a][1,4]benzodiazepine;
10-trifluoromethyl-1-[(dimethylamino)methyl]-4-methyl-6-(2,6-difluorophenyl)-4H-imidazo[1,2-a][1,4]benzodiazepine;
8-chloro-1-[(methylamino)methyl]-4-methyl-6-(o-chlorophenyl)-4H-imidazo[1,2-a][1,4]benzodiazepine;
8-nitro-1-[(methylamino)methyl]-4-methyl-6-phenyl-4H-imidazo[1,2-a][1,4]benzodiazepine;
8-nitro-1-[(methylamino)methyl]-4-methyl-6-(o-chlorophenyl)-4H-imidazo[1,2-a][1,4]benzodiazepine;
8-trifluoromethyl-1-[(methylamino)methyl]-4-methyl-6-phenyl-4H-imidazo[1,2-a][1,4]benzodiazepine;
8-trifluoromethyl-1-[(methylamino)methyl]-4-methyl-6-(o-chlorophenyl)-4H-imidazo[1,2-a][1,4]benzodiazepine;
8-fluoro-1-[(methylamino)methyl]-4-methyl-6-(o-chlorophenyl)-4H-imidazo[1,2-a][1,4]benzodiazepine;
8-chloro-1-[(methylamino)methyl]-4-methyl-6-(2,6-difluorophenyl)-4H-imidazo[1,2-a][1,4]benzodiazepine;
8-fluoro-1-[(methylamino)methyl]-4-methyl-6-(2,6-difluorophenyl)-4H-imidazo[1,2-a][1,4]benzodiazepine;
9-bromo-1-[(methylamino)methyl]-4-methyl-6-(o-chlorophenyl)-4H-imidazo[1,2-a][1,4]benzodiazepine;
7-chloro-1-[(methylamino)methyl]-4-methyl-6-(o-chlorophenyl)-4H-imidazo[1,2-a][1,4]benzodiazepine;
10-trifluoromethyl-1-[(methylamino)methyl]-4-methyl-6-(2,6-difluorophenyl)-4H-imidazo[1,2-a][1,4]benzodiazepine; and the like.

The pharmacologically acceptable acid addition salts of compounds of formula XXIV (including XXIVA, XXIVB, and XXIVC) can be prepared and isolated by conventional processes, such as reacting a compound of formula XXIV with a selected pharmacologically acceptable acid. Such acids include hydrochloric, hydrobromic, phosphoric, sulfuric, acetic, tartaric, lactic, citric, malic, maleic, methanesulfonic, benzenesulfonic, cyclohexanesulfamic acids, toluenesulfonic, and the like. The reaction is conveniently performed in an organic solvent, e.g., ether, dioxane or tetrahydrofuran, ethanol, methanol, ethyl acetate; the salts can be recovered by crystallization, precipitation or evaporation of the solvent. These salts are useful in the same manner as the free base.

I claim:
1. A compound of the formula

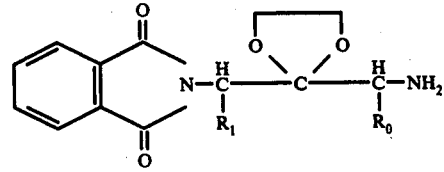

wherein $R_0$ and $R_1$ are hydrogen, methyl or ethyl.

2. A compound of the formula:

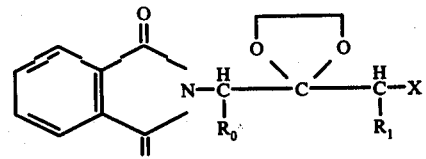

wherein X is bromo, chloro, $N_3$, or

and wherein $R_0$ and $R_1$ are hydrogen, methyl, or ethyl.

3. A compound according to claim 2 wherein X is bromo.

4. A compound according to claim 2 wherein X is -$N_3$.

* * * * *